United States Patent [19]

Wenger

[11] 4,177,669
[45] Dec. 11, 1979

[54] DEVICE FOR MEASURING THE DENSITY OF A FLUID
[75] Inventor: Alfred Wenger, Langenbruck, Switzerland
[73] Assignee: Institut Straumann AG, Switzerland
[21] Appl. No.: 925,751
[22] Filed: Jul. 18, 1978
[30] Foreign Application Priority Data
Jul. 27, 1977 [CH] Switzerland ............... 9278/77
[51] Int. Cl.$^2$ ............................................. G01N 9/00
[52] U.S. Cl. ............................................. 73/32 A
[58] Field of Search ............................... 73/32 A, 30
[56] References Cited
U.S. PATENT DOCUMENTS
4,037,459  7/1977  Schlatter ..................... 73/32 A
4,064,739  12/1977  November et al. ........... 73/32 A Primary Examiner—James J. Gill
Attorney, Agent, or Firm—McGlew and Tuttle

[57] ABSTRACT

The device includes an oscillation body and an electronic circuitry component connected to an oscillation detector and to plural oscillation generators, and including a period of frequency meter, phase shifters supplying the generators with an excitation signal shifted in phase relative to the detector signal, and a modulator. The phase angle between the detector and excitation signals, and the oscillating frequency, are varied substantially periodically within a given interval at a frequency which is lower than the oscillation frequency. Control elements control the phase and frequency position of the interval as a function of the variation of the ratio of the detector signal to the excitation signal, and of the relation between the variations, within the interval, of the detector and excitation signals and the phase angle therebetween.

10 Claims, 9 Drawing Figures

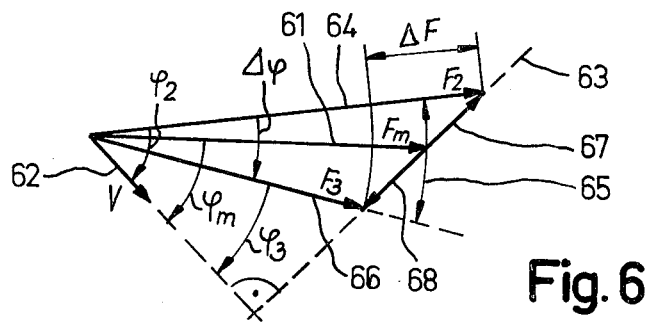
Fig. 6
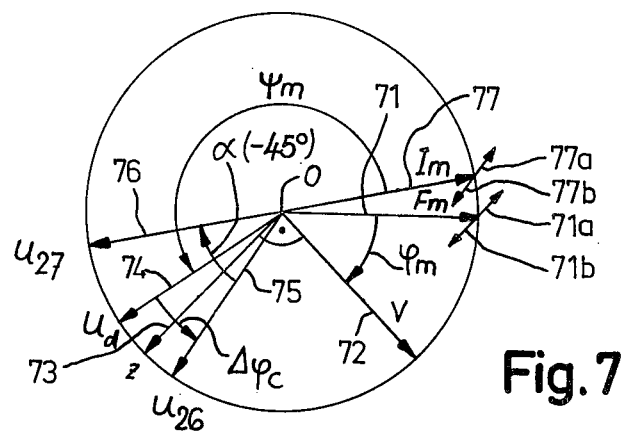
Fig. 7
Fig. 8

DEVICE FOR MEASURING THE DENSITY OF A FLUID

FIELD AND BACKGROUND OF THE INVENTION

This invention relates to a device for measuring the density of a liquid or gaseous medium, comprising a support by which an oscillating body to be introduced into the medium is held in a position permitting its oscillation, at least one oscillation detector for producing, during operation of the device, a detector signal depending on the oscillation of the body, at least one oscillating generator for exciting the oscillating body, and electronic circuitry connected to the oscillation detector and oscillating generator and including a period meter or a frequency meter for determining the period or frequency of oscillation, and at least one phase shifter for supplying the oscillation generator with an excitation signal shifted in phase, through a phase angle, relative to the detector signal produced by the oscillation detector. More particularly, the present invention is directed to an improved device, of this type, for measuring the density of a liquid or gaseous medium.

DESCRIPTION OF THE PRIOR ART

In numerous processes, it is required to measure the density of liquid or gaseous substances continuously or quasi-continuously. It is known that the resonance frequency of an oscillating solid body surrounded by an ideal liquid or ideal gas depends on the density of the liquid or gas. Therefore, it is possible to reduce a density measurement to a period or frequency measurement. The density can be calculated from the resonance period or frequency. If, instead of an ideal, non-viscous medium, the body oscillates in a viscous medium, a frictional force acts on the oscillating body, due to the viscosity. As compared to the oscillation in an ideal medium, the viscosity results in a reduction not only of the quality factor but also of the resonance frequency. Now, if the density were to be calculated from this reduced resonance frequency while using the same formula as for an ideal medium, a major or minor error would ensue, depending on the viscosity.

A device is known from British Pat. No. 991,736, which comprises an oscillating body in the form of a hollow cylinder executing torsional oscillations during the measurement, an oscillation generator, an oscillation detector, and electronic circuitry having its input connected to the oscillation detector and its output to the oscillation generator. The oscillation detector comprises a coil in which, during the oscillation, a voltage proportional to the oscillation velocity is induced. The oscillation generator is provided with a solenoid. The electronic circuitry comprises, among other elements, a phase shifter producing a phase shift of 45° between the energizing voltage, applied to the oscillation generator, and the detector voltage, delivered by the oscillation detector. This may partly compensate for the displacement of the resonance frequency caused by the viscosity, since the frictional force due to the viscosity lags the deflection by a phase angle of 45° and, consequently, the velocity by a phase angle of 135°. If the excitation force now leads the oscillation velocity by 45°, the force produced by the viscosity can be compensated. The density of a viscous medium may then be calculated by substituting the frequency resulting from the mentioned phase shift for the resonance frequency in the formula valid for a non-viscous medium.

The device of the prior art, however, is affected by still another source of error. Even if the phase shift between the detector voltage and the energizing voltage is set to 45°, in general, the excitation force does not lead the oscillation velocity by a phase angle of exactly 45°. That is, eddy currents are produced in the oscillating body, in the oscillation detector, and in the oscillation generator, which may cause further phase shifts between the oscillation velocity and the detector voltage, and between the energizing voltage and the excitation force. The eddy currents depend on the frequency and on the conductivity of the conductor materials through which they flow. The conductivity, in turn, depends on the temperature. Thus, the phase shift produced by the eddy currents depends both on the temperature and the frequency and cannot be compensated by a fixed phase shift additionally produced by the electronic part. This leads to measuring errors. Even if no electromagnets are provided in the oscillation generators or in the oscillation detectors, parasitic phase shifts due to various effects are produced.

SUMMARY OF THE INVENTION

The invention is directed to a device for measuring the density of a fluid and in which measuring errors, caused by parasitic phase shifts are eliminated.

For this purpose, the electronic circuitry of the invention device comprises means for varying both the phase angle, formed between the detector signal and the excitation signal, and the oscillation frequency, at least approximately periodically within a given interval and at a frequency which is lower than the oscillation frequency of the oscillating body, and with the electronic circuitry further comprising control elements controlling the phase and frequency position of the interval as a function of the variation of the ratio of the detector signal to the excitation signal, and of a relation between the variations, occurring within such interval, of the detector signal, the excitation signal, and the phase angle formed between the detector signal and the excitation signal.

As explained in the foregoing, because of the parasitic phase shifts, it is not possible to infer the exact phase positions of the oscillation velocities and excitation forces from the phase positions of the electric detector and energizing signals. The invention is based on the finding that, instead of measuring the phase shift between the corresponding alternating voltages, the actual phase shift between the excitation force and the oscillation velocity may also be ascertained by modulating the phase and determining the variations occurring in this connection. These variations are largely independent of the parasitic phase shifts and, consequently, make it possible, while using a relationship based on an equation, to find out and determine, without an appreciable error, the phase shift between the oscillation velocity and the excitation force.

For this purpose, the electronic circuitry is of such design that the phase at which the oscillation period is to be measured comes to lie, at least approximately, in the center of the modulation interval. This makes it possible, as will be explained hereinafter in the description of a particular embodiment, to determine the density in a quasi-continuous manner from averaged oscillation periods, which can be done with simple circuit means.

The conditions to be satisfied during the modulation may be expressed by a differential equation. Now, of course, the variations occurring during the modulation are not differential or infinitesimal, but of finite dimension. It would also be possible, with a small modulation swing, to introduce finite differential quantities into the differential equation, instead of the infinitesimal ones. The differential equation would then still be approximately satisfied.

However, as will be shown in the description hereinafter, it is possible to design the phase modulator and the phase controller in such a manner that, for a specific point falling within the modulation interval, the differential equation is satisfied exactly at any deviation of the phase. This may be obtained by a modulation such that the two sides of the differential equation are always equal to zero.

Still another aspect, however, is to be considered. By a phase shift of 45° between the excitation force and the oscillation velocity, the errors which are produced in first approximation by the viscosity can be compensated. However, experience has shown that, with an extremely high viscosity and a correspondingly low quality factor of the oscillator, it is advantageous to carry out the measurement at a phase shift not of 45°, but one of somewhat smaller value. The maximum deviation from 45° in such a case is to be about 5°.

An object of the invention is to provide an improved device for measuring the density of a fluid.

Another object of the invention is to provide such a device in which measuring errors caused by parasitic phase shifts are eliminated.

A further object of the invention is to provide such a device including an improved electronic circuitry.

For an understanding of the principles of the invention, reference is made to the following description of a typical embodiment thereof as illustrated in the accompanying drawings.

BRIEF DESCRIPTION OF THE DRAWINGS

In the Drawings:

FIG. 6 is a polar coordinate diagram showing the modulation;

FIG. 7 is a polar coordinate diagram showing the phase relationship between the individual oscillation quantities and the electric signals during the modulation;

FIG. 8 is a diagram showing the different electric signals and a phase angle as a function of time.

DESCRIPTION OF THE PREFERRED EMBODIMENT

Figure 1:
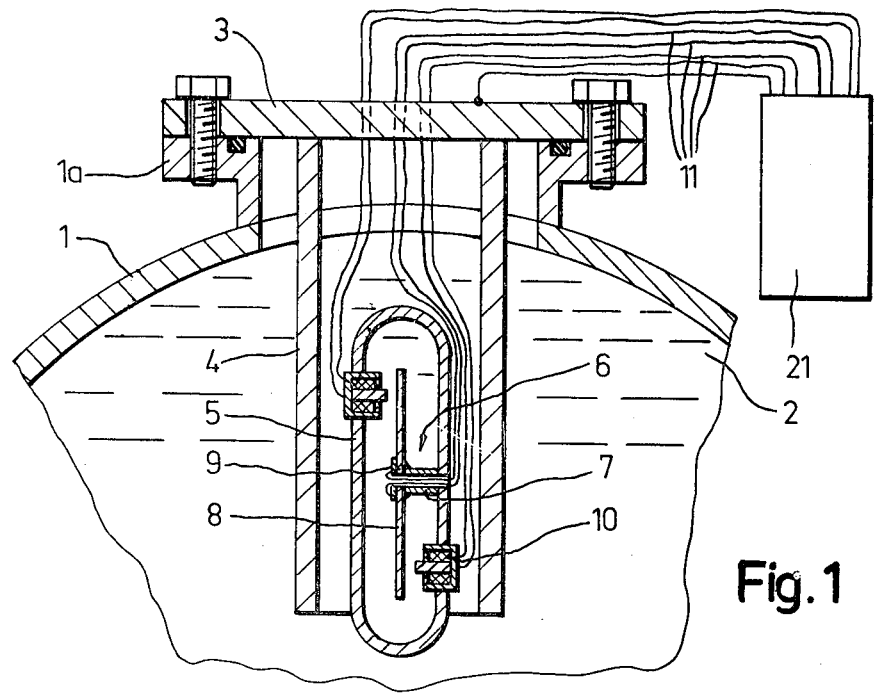
FIG. 1 is a diagrammatical sectional view of a device for measuring the density of a fluid.

FIG. 1 shows a device for measuring the density of a medium, more particularly, of a liquid 2. For example, in the course of an industrial process, the liquid may flow through a tube 1 provided with a flange 1a. Another, tightly closing, flange 3 is removably secured to flange 1a. A supporting structure 4 is secured to flange 3 and projects into the interior of tube 1. Structure 4 carries a flat tubular piece 5 which extends parallel to tube 1 and is open on both of its ends. A mounting support 6 comprising a hollow cylindrical stud 7 is secured to tubular piece 5. To the left end of stud 7, as viewed in FIG. 1, an oscillating body 8 is fixed, for example, brazed. Oscillating body 8 comprises a plane, circular plate made, preferably, of a rolled, thermo-compensated alloy such as frequently employed in the watch-making industry for manufacturing spiral springs. Thermo-compensated, in this connection, means that the modulus of elasticity E is approximately constant within a wide temperature range. Support 6 holds the oscillating body 8 in the center thereof, to permit oscillation.

A passage opening is provided in the center of oscillating body 8. On the outside of oscillating body 8, i.e., the side remote from stud 7, a multiple oscillation detector 9 is mounted. This detector comprises an annular piezoelectric crystal 9a (FIG. 5) resting by one of its surfaces on oscillating body 8 and being electrically connected thereto. To the other surface of crystal 9a, segmental electrodes 9b uniformly distributed over the circumference are secured.

The device further comprises six oscillation generators 10 which are secured to tubular piece 5, three at each side of oscillating body 8. To simplify the drawing, only two of oscillators 10 are shown in FIG. 1. Each oscillation generator 10 comprises a ferromagnetic pot and a cylindrical permanent-magnet core extending along the pot axis. The free end of the magnet faces the oscillating body 8, with a gap left therebetween. The pot accommodates a winding surrounding the core and is provided with, preferably, a non-magnetic cover tightly sealing the winding to the outside.

Figure 5:
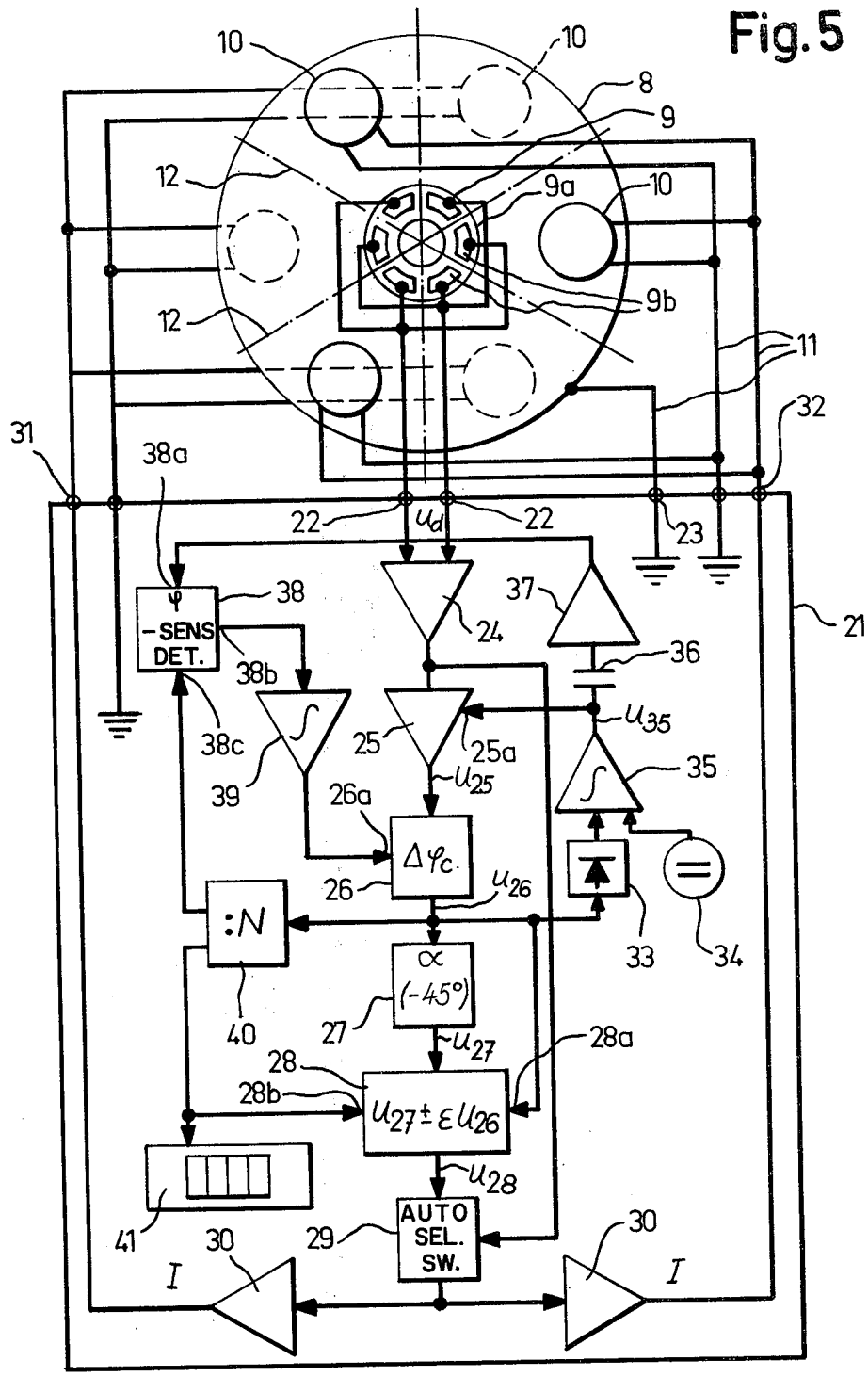
FIG. 5 is a diagrammatical top view of the oscillating body showing the arrangement of the oscillation detectors and generators, along with a block diagram of one embodiment of the electronic circuitry.

Support 6, oscillation detector 9 and oscillation generators 10 are connected through electric conductors 11 to an electronic part 21. The two conductors for connecting oscillation detector 9 are passed through a hole in tubular piece 5, and through the passage opening in the center of oscillating body 8 and the hollow stud 7. The conductors connected to the oscillation detector and to the oscillation generators extend through tight lead-ins provided in flange 3. The block diagram of electronic part 21 and the terminals of conductors 11 are shown in FIG. 5.

While carrying out a measuring operation, body 8 executes flexural oscillations. The two groups of oscillation generators 10, each comprising three generators arranged along and aligned with a single pitch circle of the oscillating body and spaced from each other by 120°, with the generators of one group alternating with those of the other group, make it possible to excite an oscillation of the third order, so that three nodal lines 12 are produced which intersect in the center of oscillating body 8 with each forming diametral lines and by which the oscillating body is subdivided into six sectors. The oscillation detector 9 is secured to the oscillating body in a manner such that one electrode 9b is located in each sector.

The electronic circuitry comprises an input with two terminals 22. Each terminal is connected to three electrodes 9b of oscillation detector 9. Support 6 and, consequently, also oscillating body 8 and the adjacent surface of crystal 9a, are connected to a terminal 23 of electronic circuitry 21, which is grounded. The two input terminals 22 are connected to the inputs of a differential amplifier 24 whose output is connected to the input of an amplifier 25 having a variable gain. The output of amplifier 25 is connected to the input of a controllable phase shifter 26, the output of which is connected to the input of another phase shifter 27, producing a constant phase shift $\alpha$ of $-45°$. Phase shifter 27 is followed by a modulator 28 and an automatic selector switch 29. The output of the latter is connected to the inputs of two amplifiers 30 having their outputs connected to respective output terminals 31 and 32. Each of these terminals is connected to one winding terminal of three oscillation generators 10. The other winding terminals of the oscillation genterators may be grounded. Amplifiers 30 are of a design such that they supply oscillation generators 10 with an alternating current forming the energizing signal which is in phase with the voltage applied to the input of amplifier 30.

The output of controllable phase shifter 26 is, in addition, connected to the terminal 28a of modulator 28 and to a rectifier 33. The output of the rectifier is connected to one input of an integrator 35 whose other input is connected to a reference voltage source 34. The output of integrator 35 is connected to the control terminal 25a of variable amplifier 25 and, through a capacitor 36 and an amplifier 37, to the terminal 38a of a phase-sensitive detector 38. The output 38b of the detector is connected through an integrator 39 to the control terminal 26a of phase shifter 26.

Also provided is a timing unit 40 having its input connected to the output of phase shifter 26 and its outputs to the terminal 28b of modulator 28 and to the terminal 38c of detector 38. Timing unit 40 substantially comprises a frequency divider reducing the frequency of the supplied voltage by a factor N. Finally, a period meter 41 is provided, which is formed by a time counter, which is connected, for example, to the output of timing unit 40 and may be equipped with, or connected to, a printer.

The operation of the device is explained, in principle, in the following.

Upon starting the operation of the device, oscillating body 8, oscillation detector 9, oscillation generators 10 and electronic circuitry 21, together form an oscillator. Initially, let there be carried out a conceptional experiment. Assume that tube 1 does not contain any liquid, and that it is tightly sealed and evacuated. The flexural oscillations executed by oscillating boy 8 are expressed by a partial differential equation. The differential equation comprises terms for the following forces: the inertia force, the frictional force produced by the friction in the material of the plate and by the support, the restoring elastic force, and the excitation force produced by the oscillation generators. In accordance with the differential equation, these forces must compensate each other at any instant. During operation, the individual elements of the oscillating body execute vertical oscillations, with the amplitude being a harmonic function of the time t. Consequently, all of the forces are also harmonic functions of the time.

As is well known, oscillation problems may be solved in a particularly simple manner by means of complex numbers. The various variables involved in an oscillation may then be represented as projections of vectors which rotate at the cyclic frequency about the origin of the plane of complex numbers.

Figure 2:
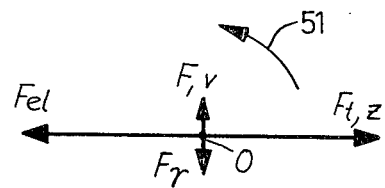
FIG. 2 is a vector diagram showing the phase relationship for a body oscillating at its natural frequency in a vacuum.

FIG. 2 shows a vector diagram to illustrate the phase relationship in a plate-shaped oscillating body 8 vibrating in vacuum at its natural frequency. FIG. 2 shows four vectors which rotate at the same angular velocity, namely, corresponding to the cyclic frequency of the oscillation, about the coordinate origin O and in the direction indicated by arrow 51. Each of the four vectors is associated with one of the four forces. By projecting the four vectors on a fixed coordinate axis, the variation in time of the forces is obtained. The vectors, which may also be conceived as complex numbers, are indicated by letter symbols which, in the following, will partly also be used for designating the amplitudes of the respective quantities.

Thus, F indicates the amplitude of the excitation force, $F_t$ the amplitude of the inertia force, $F_{el}$ the amplitude of the elastic force and $F_r$ the amplitude of the frictional force. Further, z designates the amplitude of the deflection, and v the amplitude of the velocity of the elements of the oscillating body. The inertia force is in phase with the deflection of the elements of the plate from their rest position. The excitation force is in phase with the velocity of the elements of the plate and leads the inertia force by 90°. The elastic force is in opposition to the deflection, thus displaced by 180° relative to the inertia force. The frictional force is in opposition to the velocity, thus displaced through 180° relative to the excitation force.

Let there now be carried out another conceptional experiment in which the liquid 2 to be measured has been introduced into tube 1 and the plate is again set in oscillation. Since, in this case, a part of the liquid 2 oscillates along with oscillating body 8, the inertia force will be greater than with an oscillation in vacuum. Let is be assumed, first, that the liquid has no viscosity and oscillating body 8 vibrates at its resonance frequency which is now lower than the resonance frequency experienced in vacuum. Let $f_{id}$ be the resonance frequency obtained in an ideal medium in accordance with the conceptional experiment, and $T_{id}$ the length of the period, i.e., the reciprocal value thereof. Further designations would be k for a constant, and $f_v$ and $T_v$ for the resonance frequency obtained in a vacuum, and the reciprocal length of a period, respectively. The density of liquid 2 may then be calculated in accordance with the following relation:

$$D = k\,((T_{id}/T_v)^2 - 1) \qquad (1)$$

The relation (1), however, applies only to an ideal liquid without viscosity. If the liquid is viscous, the viscosity not only reduces the quality factor but, in addition, also reduces the resonance frequency.

This means that formula (1) would calculate a too high density. That is, with oscillating body 8 vibrating in a viscous liquid, still another term must be included in the differential equation describing the oscillation, namely, a term for the viscous force having an amplitude $F_{vis}$. In chapter 2, section 24, of the publication "Hydrodynamik" by L. D. Landau and E. M. Lifschitz, Akademie-Verlag, Berlin, 1966, there are analyzed the conditions for a plate executing a translatory oscillation in the plane of its extension. It may be inferred from the results that, with a flexural oscillation, the viscous force leads the frictional force, produced by the internal friction and the support, by 45°.

Figure 3:
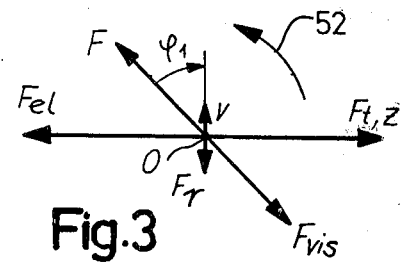
FIG. 3 is a vector diagram showing the phase relationship for a body oscillating in a viscous liquid.

This is shown in the vector diagram of FIG. 3, where arrow 52 indicates the direction of rotation of the vectors which produce the forces included in the differential equation. With a suitable design of oscillating body 8, its support 6, detector 9 and oscillation generators 10, it may then be obtained that amplitude $F_r$ of the frictional force is very small, substantially smaller than amplitude $F_{vis}$ of the viscous force.

In the event that the viscous force is substantially greater than the frictional force, its influence may be compensated, in a first approximation, by advancing the excitation force through a phase angle of 45° relative to the velocity. Then, the excitation force leads the deflection by a phase angle of 135°. The phase angle by which the velocity is displaced relative to the excitation force is generally designated $\phi$ in the following. While counting $\phi$ as positive in the direction of rotation of arrow 52, the phase angle, in the present specific case, is negative and has the value $\phi_1 = -45°$. Oscillating body 8 now oscillates at the frequency $f_1$ at which the excitation force at least approximately compensates the viscous force. If now, in the relation (1), the measurable length $T_m$ is substituted for $T_{id}$, the relation $$D = K((T_m/T_v)^2 - 1) \tag{2}$$

is obtained. Then, while measuring a viscous liquid, if the period length resulting from a phase shift $\phi_1 = -45°$, which length is a reciprocal of frequency $f_1$, is substituted for period length $T_m$, the correct density is obtained in a satisfactory approximation. The period length in vacuum $T_v$, and constant k, may be determined by means of standard liquids. Thus, it is unnecessary to actually carry out a measurement in vacuum.

In practice, however, as has already been mentioned above, it is not possible to produce a phase shift, between the oscillation velocity and the excitation force corresponding exactly to the predetermined value, only by means of a phase shifter causing a fixed phase shift. For example, if oscillation detectors and generators with coils are used, the eddy currents cause frequency-dependent phase shifts. If piezoelectric oscillation detectors and generators are used, the dielectric losses also result in frequency-dependent phase shifts. In addition, the amplifiers and other elements connected in the electronic part possess frequency-dependent impedances which may lead to phase errors.

Figure 4:
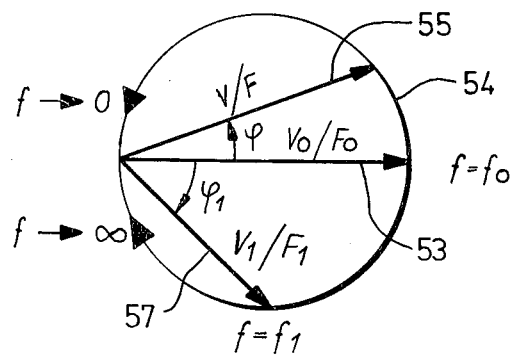
FIG. 4 is a polar coordinate diagram showing the amplitude relationship between the oscillation velocity and the excitation force as a function of the phase shift between these two quantities.

However, the phase position can be determined and defined by the evaluation or determination of differential quantities. This will be explained in the following. It can be evidenced that for any forced oscillation characterized by a linear second-order differential equation with constant coefficients, the following relation is valid:

$$v/F = (v_0/f_0) \cos \phi \tag{3}$$

wherein v and F are the amplitudes of the oscillation velocity and the excitation force, respectively, at a phase angle $\phi$. Further, $v_0$ and $F_0$ are the amplitudes of the oscillation velocity and the excitation force, with these variables in phase, i.e., while the phase angle $\phi$ equals zero. This relation is illustrated in FIG. 4. The diagram of FIG. 4 shows a vector 53 of the length $v_0/F_0$ and having its end points on a circle 54 and forming a diameter of the circle. Any vector 55 whose starting point coincides with that of vector 53 and whose end point is on circle 54 represents a possible stage of oscillation. The angle between vectors 55 and 53 is equal to the phase angle $\phi$ and the magnitude of the vector equals the amplitude ratio v/F. With the phase angle going toward $+90°$, the frequency approaches the value zero. With the phase angle going toward $-90°$, the frequency tends to infinite values. As a specific case, still another vector 57 is shown in FIG. 4, having a phase angle $\phi$ of the value of $\phi_1 = -45°$. The corresponding frequency is $f_1$ and the ratio between the amplitudes of the oscillation velocity and the excitation force is $v_1/F_1$.

Upon solving with respect to v and differentiation, the following value results for the differential dv from the relation (3):

$$dv/v = dF/F - tg\phi \, d\phi \tag{4}$$

With the substitution of the value $\phi_1 = -45°$ for phase angle $\phi$ in the term of the righthand side of formula (4), the differentials satisfy the following equation:

$$dv/v = (dF/F) + d\phi \tag{5}$$

Formulas (4) and (5) determine an oscillation stage with a specific phase angle, in a well-defined manner, by differential values. In particular, formula 5 determines the oscillation stage in which the oscillation velocity lags the excitation force by a phase angle of 45°. Now, of course, the oscillation values appearing in equations (4) and (5) again cannot be determined directly, but only through the associated electric signals.

Therefore, equations (4) and (5) are replaced by the differential equations $$dU/U = (dI/I) - (tg \, \alpha \, d\Psi) \tag{4a}$$

$$dU/U = (dI/I) + d\Psi \tag{5a}$$

In these equations, dU is the differential variation of the amplitude U of an electric detector signal furnished by an oscillation detector. Depending on the kind of the employed detector, the detector signal may be proportional to the oscillation velocity or to the deflection of the oscillating body. If, as in the present embodiment, an oscillation detector with a piezoelectric crystal is employed, the detector signal is proportional to the deflection. Further, dI is the variation of the amplitude I of an electric energizing signal producing the excitation force. The differential $d\Psi$ equals the differential variation of the phase angle $\Psi$ through which the detector signal is displaced relative to the energizing signal producing the excitation force. With a given modulation, the differential variations $d\Psi$ of phase angle $\Psi$ are identical for both kinds of detector signals. The value of phase angle $\Psi$, on the contrary, differs by 90° for the two kinds of detector signals, corresponding to the phase shift between the oscillation deflection and the oscillation velocity. While operating with a detector signal representing the velocity, the phase angle $\Psi$, under ideal conditions, would be equal to phase angle $\Psi$. In fact, however, due to the mentioned parasitic phase shifts, the phase angle value, in general, is somewhat different. As compared thereto and in practice, no difference results therefrom for the differential variations, so that independently of the kind of the detector signal, $d\Psi = d\phi$.

Equation (4a) further differs from equation (4) in that the angle $\alpha$ is substituted for phase angle $\phi$. Angle $\alpha$ is also termed the modulation angle in the following. The modulation angle $\alpha$ is predetermined by a circuit of the electronic circuitry, as will be explained hereinafter. As will also be explained later, modulation angle $\alpha$ is approximately equal to the phase angle $\phi_m$ at which the measuring of the density is carried out.

Thus, in principle, a phase angle can be determined by taking differential values. Further, by taking or determining the differential variations, a definite, predetermined phase position may be adjusted. In an actual measuring or controlling operation, however, differential, i.e., infinitesimal, variations cannot be handled, only variations of finite magnitude. Of course, there is still a possibility of operating with relatively small variations and to introduce them into equations (4) or (5) or (4a) or (5a) instead of the differential values. Then, the differential equations are no longer exact, but are still satisfied approximately. There is a possibility, however, to vary the phase angle $\phi$, the amplitude v of the oscillation velocity, and the amplitude F of the excitation force within such a finite interval that, for a predetermined location falling within the interval, the differential equations (4), (5) are exactly satisfied.

This will now be explained in the following, while starting from equations (5), (5a) and considering a specific case. That is, the electronic circuitry or component is of such design that the amplitude v of the oscillation velocity remains constant and, consequently, both sides of equation (5) or (5a) disappear identically. In FIG. 6, at 61, a vector representing the excitation force is shown having its length equal to that amplitude $F_m$ of the excitation force, which corresponds to the oscillation stage in which the oscillation velocity lags the excitation force by a phase angle of approximately 45°. At this stage, phase angle $\phi$ has the value $\phi_m$ which approximately equals $-45°$. Vector 62 represents the oscillation velocity and its length v is equal to the velocity amplitude and has to remain constant, in accordance with the prerequisite. Also shown in FIG. 6 is a straight line 63 which is perpendicular to vector 62 and passes through the end point of vector 61. Thus, line 63 forms an angle of about 45° with vector 61.

Now, the excitation force is changed to be represented by vector 64 having an identical origin with vectors 61 and 62 and having its end point on straight line 63. The length of this vector is equal to the magnitude of the instantaneous amplitude $F_2$ of the excitation force, and the angle between vectors 62 and 64 and equals the instantaneous phase angle $\phi_2$. FIG. 6 further shows another vector 66 representing the excitation force at another oscillation stage. The length of vector 66 is equal to the amplitude $F_3$ of the excitation force at the respective stage, and the angle between vectors 62 and 66 is equal to the associated phase angle $\phi_3$. Also shown in FIG. 6 is the differential vector 67 of the two vectors 61 and 64 and the differential vector 68 of the two vectors 61 and 66. Phase angles $\phi_2$ and $\phi_3$ are chosen so as to obtain identical values for differential vectors 67 and 68.

It can be proved that amplitude v of the velocity remains constant for any phase angles $\phi$, provided that the vector representing the excitation force is varied so that its end point follows straight line 63. This is clearly due to the fact that, in phase relation, the differential vectors 67 and 68, which represent vectorial changes of force, extend at a right angle to the oscillation velocity and, therefore, do not change the energy of oscillation.

FIG. 6 further shows an element of arc 65 passing through the end point of vector 61, and the angle difference $\Delta\phi = \phi_2 - \phi_3$ associated therewith. The length of the element of arc 65, which is measured in the same units as the length of the vectors, is given by the formula $$\Delta s = F_m |\Delta\phi| \tag{6}$$

For small differences of the two phase angles, the following relation is obtained for the difference $\Delta F$ between the amplitudes of the two excitation forces:

$$F_2 - F_3 = \Delta F \simeq -F_m \Delta\phi \tag{7}$$

If an infinitesimal partial interval of the variation interval in the neighborhood of vector 61 is considered, differentials can be substituted for the differences in relation (7), and the approximative sign can be replaced by an equals sign. Thus, while forming the limit values, i.e., passing to an infinitesimal partial interval, $\Delta\phi$ and $\Delta\Psi$ can be made equal to each other. Also, $\Delta F/F_m$ is then equal to $dI/I$. It results therefrom that the value of the righthand side of equation (5a) is zero. In other words, within an interval of finite magnitude, the phase angle can be varied in a manner such that the velocity amplitude remains constant and that, for an infinitesimal partial interval of the variation interval, namely, the partial interval comprising vector 61, the differential equation (5) is exactly satisfied.

If, to calculate the density, it is desired to measure the period length at a phase angle $\phi_m$ of approximately $-45°$, it is now possible to proceed in such a manner that phase angle $\phi$ is modulated and made alternately larger and smaller than $\phi_m$, namely, made alternately and periodically equal to $\phi_2$ and $\phi_3$, and at the same time, amplitude F of the excitation force is varied to assume values $F_2$ and $F_3$. In addition, if then the two time intervals, during which the phase angle assumes the values $\phi_2$ or $\phi_3$, are suitably extended, the average oscillation period during a full phase variation cycle will be exactly equal to the period length at phase angle $\phi_m$.

Some disturbing effects and corrections will be discussed in addition, in the following. As already mentioned, the differential equations (4) and (5) are valid for an oscillatory motion in which the forces occurring during the oscillation are characterized by a linear second-order differential equation with constant coefficients. Actually, however, the coefficient of friction appearing in the differential equation of the oscillation is not exactly constant but depends, for example, on the frequency. This is the main reason for the fact that the median value $\phi_m$ about which phase angle $\phi$ oscillates during the modulation is not exactly identical with the angle $\alpha$. If an oscillation detector is used which, as oscillation detector 9, furnishes a detector signal proportional to the deflection of oscillating body 8 and satisfies equation (4a) for this detector signal, the relation between $\phi_m$ and $\alpha$ is given by the formula $$\phi_m = \alpha + 3/(4Q) \tag{8}$$

If, on the other hand, equation (4a) would be satisfied for a detector signal proportional to the oscillation velocity of the oscillating body, the relation whould be given by the formula $$\phi_m = \alpha + 1/(4Q) \quad (9)$$

Q in formulas (8) and (9) is the quality factor of oscillating body 8 which oscillates in the fluid.

Thus, if, for example, a value $\alpha = \pi/4$ is preset for the modulation angle, the measurement is carried out at somewhat different values $\phi_m$. The difference is relatively small, however. That is, depending on the kind of the fluid to be measured, the quality factors for liquid and gaseous media range between about 10 and 10,000 and are greater than 20 in the cases important in practice.

It is further to be shown that, advantageously, the phase angle $\phi_m$ about which phase angle $\phi$ oscillates during the modulation, is not exactly $-45°$, but somewhat smaller.

While a viscous fluid flows past a body, the viscosity takes effect substantially only within a so-called boundary layer. To this, reference is made to the already cited publication by Landau and Lifschitz, for example. With an oscillating body, the thickness d of the boundary layer is of the order of magnitude of $$d = \sqrt{(2\eta/D\omega)} \quad (10)$$

wherein $\eta$ is the viscosity, D the density of the fluid, and $\omega$ the cyclic frequency of the oscillating body. The influence of the viscosity on the resonance frequency may now be expanded with respect to the ratio d/a, wherein a is the characteristic dimension of the oscillating body, for example, the diameter.

A value a=40 mm has been chosen in the present example. With water as the flowing luid, the ratio d/a may have the balue of about 0.0002. But for glycerol, the ratio amounts to 0.008. Now, it can be evidenced that the error caused by the viscosity is compensated, to first order in d/a, if the velocity is displaced relative to the excitation force by a phase angle of $-45° = -\pi/4$. If, however, a higher accuracy is desired and the term of second degree $(d/a)^2$ is also taken into account in the expansion, it is found that the phase angle as a function of the viscosity must be made somewhat smaller than $\pi/4$. That is, to obtain a quite exact measured value, the phase angle should have the following optimum value:

$$\phi_{opt} = -(\pi/4 - G/Q) \quad (11)$$

wherein G is a number depending on the geometry of the oscillating body and of order of magnitude 1. The quality factors for fluids range between about 10 and 10,000, depending on the kind of the fluid to be measured. Therefore, the optimum phase angles range between about 40° and 45°.

If the value of the modulation angle $\alpha$ is fixed to $-\pi/4$, whereby the equation (5a) is satisfied, the value $\phi_m$ resulting from both equation (8) and equation (9) is very close to the optimal value $\phi_{opt}$. That is, in both cases, the remaining deviation from the optimum value of the phase angle is of the order of magnitude of $Q^{-2}$, if arc measures of the angles are taken. Consequently, it is possible to use a modulation angle of $\alpha = -45°$ both with a detector producing a signal proportional to the oscillation velocity of the oscillating body, and with a detector producing a signal proportional to the deflection of the oscillating body.

A further remark is to be added concerning the unit angles. In the foregoing, the angles have been indicated partly in circular measure, partly in degrees. In the formulas (4), (4a), (5), (5a), (6), (7), (8),a (9), and (11), also other physical quantities are involved, aside from the angles. In these formulas, the angles and angle differentials are to be introduced in circular measure.

In the following, the operation of the electronic part 21 is explained with reference to FIGS. 7 and 8. FIG. 7 shows a plurality of vectors representing the various physical quantities occurring during the operation of the device. The lengths of the vectors correspond to the amplitudes of the respective quantities. The instantaneous values of the quantities result from the projection of the vectors on a fixed straight line while the vectors rotate counterclockwise at the cyclic frequency about the coordinate origin O. Vector 71 represents an intermediate value of the excitation force whose amplitude F at the respective stage has the value of $F_m$. Vector 72 represents the oscillation velocity having the amplitude v, which is displaced relative to the intermediate value of the excitation force by the phase angle $\phi_m$. Vector 73 represents the deflection of the elements of oscillating body 8 from their rest position, which lags the oscillation velocity by 90° and has an amplitude of the value z. Vector 74 represents the detector signal $U_d$ having the amplitude U. Vector 75 represents the output voltage $U_{26}$ of the controllable phase shifter 26. Vector 76 represents the output voltage $U_{27}$ of phase shifter 27. Vector 77 represents an intermediate value of the energizing current the amplitude I of which has the intermediate value of $I_m$. The energizing current produces the excitation signal by which the oscillation generators 10 are excited. Also shown is the intermediate value $\Psi_m$ of angle $\Psi$ by which the detector signal is displaced relative to the excitation signal.

During the operation of the device, body 8 oscillates. Detector 9 produces an electric detector signal $U_d$, namely an alternating voltage, which is supplied to the input terminals 22 of the electronic part. The variation in time of the detector signal is shown in the uppermost partial diagram of FIG. 8. The detector signal is amplified by amplifiers 24 and 25 and delivered to phase shifter 26. Amplifier 25 is controlled by means of circuit elements 33, 34, 35 to keep the output voltage $U_{26}$ of the phase shifter constant. Under ideal conditions, the detector signal and output voltage $U_{25}$ of amplifier 25 would be in phase with the deflection of the elements of the oscillating body. In fact, however, because of parasitic voltages in the detector, and because the input impedance of the amplifiers is not infinite, and for still other reasons, they are displaced relative to the deflection. This and further phase errors are corrected by the controllable phase shifter 26, i.e., this phase shifter changes the phase angle by a correction angle $\Delta\phi_c$. The control of this correction angle will be explained later. The following phase shifter 27 again shifts the phase through the modulation angle $\alpha = -45°$. To this, it is to be noted that in FIG. 7, the angles are considered positive again in the counterclockwise direction. The output voltage $U_{27}$ of phase shifter 27 is supplied to modulator 28. Voltage $U_{26}$ is also supplied to the modulator and reduced, by means of a voltage divider, to the value $\epsilon U_{26}$, with $\epsilon$ having the value of 0.1, for example. Modulator 28 is controlled by timing unit 40 in a manner such that alternately, during one interval of time, a portion of voltage $U_{26}$ is added by the modulator to voltage $U_{27}$ and, during another interval of time, the identical portion of voltage $U_{26}$ is subtracted from voltage $U_{27}$, so that voltage $U_{28}$ appears at the output of the modulator. It may also be said that during one time interval of the modulation period, the two voltages are directly superimposed, while during the other time interval, prior to the superimposition, the phase of one of the voltages is turned through 180°. At the same time, the two time intervals are to be longer, for example, ten times longer, than the period of the oscillating body. During the interval designated $t_1$ in FIG. 8, modulator 28 is controlled by timing unit 40 in such a manner that voltage $\epsilon U_{26}$ is added to voltage $U_{27}$. This increases the amplitude and, further, reduces the phase shift between voltages $U_{26}$ and $U_{28}$. Therefore, amplitude I of the excitation current shown in the second partial diagram of FIG. 8, becomes greater than $I_m$. Accordingly, the excitation force is also increased. Further phase angle $\Psi$ shown in the third partial diagram of FIG. 8, by which the detector voltage is displaced relative to the excitation current, becomes smaller than intermediate value $\Psi_m$. Thus, starting from vectors 77 and 71 of FIG. 7, the vectors representing the excitation current and the excitation force are swung counterclockwise and extended, so that their end points move to the end points of differential vectors 77a, 71a. Phase angle $\phi$ through which the velocity is displaced relative to the excitation force changes correspondingly, i.e., becomes more negative, thus larger, than $\phi_m$. During the time interval $t_2$ of FIG. 8, voltage $\epsilon U_{26}$ is subtracted from $U_{27}$. Consequently, the vectors representing the excitation current and the excitation force are shortened relative to vectors 77 and 71 shown in FIG. 7, and swung clockwise to the end points of differential vectors 77b, 71b. As a result, the amplitude of the excitation force becomes smaller and phase angle $\phi$ becomes less negative.

Thus, the modulation causes a periodic, jump-like variation between two oscillation stages corresponding to the positions of vectors 64 and 66 of FIG. 6. Phase angles $\Psi$ and $\phi$ undergo an oscillatory variation about an intermediate value, namely, the values $\Psi_m$ and $\phi_m$. The magnitude of phase angle $\phi_m$ is given by equation (8), with the value of $-\pi/4$ introduced for the modulation angle $\alpha$. In accordance therewith, amplitude F of the excitation force oscillates about an intermediate value $F_m$. Since the modulator is controlled by a rectangular-wave signal produced by the timing unit, this intermediate value, corresponding to the variations in position, recurs for very short intervals of time. Incidentally, intermediate values $I_m$, $F_m$, $\Psi_m$, $\phi_m$ correspond approximately to the mean values of quantities I, F, $\Psi$, and $\phi$.

Modulator 28 thus modulates the phase and amplitude of the voltage $U_{27}$ supplied thereto, but not directly the frequency. The frequency, however, is also varied, indirectly. That is, modulator 28 is connected in a circuit belonging to the oscillator. Therefore, as may be learned from FIG. 4, for example, the variation of phase angle $\phi$ is connected to a variation of the oscillation frequency. In the uppermost partial diagram of FIG. 8, it is shown that the voltage produced by the oscillation detector, i.e., detector signal $U_d$, has a higher frequency during the time interval $t_1$ than during the time interval $t_2$. Besides, timing unit 40 controls the modulator 28 in such a way that time interval $t_2$ becomes longer than time interval $t_1$, namely, to an extent such that oscillating body 8 executes the same number of oscillations in either of the two intervals. In the uppermost partial diagram of FIG. 8, for illustrative purposes, the difference in frequency is exaggerated and the length of the time periods is shortened. Actually, at least 10, preferably, at least 100, sinusoidal oscillations take place in each of the two intervals of time.

The output voltage of modulator 28 is supplied, through an automatic selector switch 29, to amplifiers 30. These amplifiers are connected as controllable current sources and produce the excitation current which forms the excitation signal and is proportional to the output voltage $U_{28}$ of modulator 28. Also, amplifiers 30 are designed, and the windings of oscillation generators 10 are poled, in a manner such that the mean excitation current is in phase opposition to voltage $U_{27}$, as may be seen in FIG. 7. The excitation current produces an excitation force which, due to the already mentioned eddy currents, is displaced in phase relative to the excitation current, as shown in FIG. 7.

In the following, the operation of the control elements, comprising the controllable voltage amplifier 25 and the controllable phase shifter 26, is explained. The output voltage of phase shifter 26 is rectified in rectifier 33 and integrated and averaged in integrator 35 where it is also compared with a reference voltage furnished by a reference voltage source 34. The integration time over which integrator 35 takes the mean value covers at least some period lengths of the oscillation of oscillating body 8, but, on the other hand, is shorter than the time intervals $t_1$ and $t_2$. The control signal, i.e., the output voltage $U_{35}$ of integrator 35 is delivered to terminal 25a of amplifier 25. Thereby, this amplifier is controlled in such a manner that the amplitude of the output voltage of phase shifter 26 remains constant.

As long as the mean phase angle between the excitation force and the oscillation velocity and, thereby, also that between the excitation signal and the detector signal, have the provided optimum value, the value of amplitude z of the oscillations does not change. Since, depending on the quality factor, the oscillation conditions produced during the modulation correspond more or less to the conditions represented in FIG. 6 by vectors 64 and 66, the amplitude v of the oscillation velocity is then also approximately constant. In this case, phase shifter 26 has a strictly constant amplitude, without the necessity of varying the amplification of amplifier 25. Consequently, the control voltage furnished by integrator 35 is constant. Now, elements 36, 37, 38 and 39 are of a design such that, in this case, phase shifter 26 produces a constant phase angle correction $\Delta\phi_c$.

Let it be assumed that, first, the provided phase positions are not obtained during the modulation. Then, during the modulation, the deflection amplitude z and also the velocity amplitude v will more or less vary, depending on the magnitude of the deviation. In consequence, the control voltage delivered by integrator 35 has varying values during the two time intervals $t_1$ and $t_2$. These variations of the control voltage are supplied, through capacitor 36 and amplifier 37, to the phase-sensitive detector 38. This detector is controlled by timing unit 40 in synchronism with modulator 28. Now, phase-sensitive detector 38, in turn, produces a signal depending on the values of the voltages which are delivered thereto during the two time intervals $t_1$ and $t_2$. The signal produced by detector 38 is integrated and averaged by integrator 39, so that integrator 39 supplies to terminal 26a of phase shifter 26 a control signal. By means of this control signal, the phase angle correction produced by phase shifter 26 is varied until amplitude U of detector signal $U_d$ remains constant. In this way, by means of controllable phase shifter 26 and the control circuit associated therewith, the predetermined optimum phase position can be adjusted. It is to be noted, in addition, that detector 38 is controlled by timing unit 40 in such a manner that the detector produces signals not during the entire duration of the two intervals $t_1$ and $t_2$, but only during a part of these intervals. This is to prevent the voltage peaks which may be caused by the discontinuous variations during the modulation, from disturbing the control.

The fluids measured by means of the device may possess very different viscosities, resulting in correspondingly differing oscillation attenuations. Therefore, if the excitation forces alternately occurring during the modulation would be of equal magnitude for all fluids, very unequal oscillation amplitudes would result therefrom. That is why selector switch 29 is of a design such that it is capable of reducing the voltage supplied from the output of the modulator 28, switch 29 is controlled by the amplifier 24 in such a manner that, if voltage output of amplifier 24 is low, no reduction, or only a small reduction takes place and, if the voltage is high, the reduction is important. The switching takes place with a certain hysteresis, so that a repeated change of the switching positions during the measurement of a fluid is avoided.

By means of the period meter, the lengths of time intervals $t_1$ and $t_2$ are measured. The sum $t_1+t_2$, which is equal to the period length of the signal produced by the timing unit and controlling the modulator, is divided by the number of oscillations occurring during a modulation period, i.e., by N. The result is indicated and/or recorded. Consequently, a mean measured value $T_m$ of the period length is obtained, $$T_m = (t_1+t_2)/N \qquad (12)$$

This value can now be introduced into equation (2), to determine the density. Experience has shown that the density of liquids having a viscosity of several hundred centipoise can be measured with an accuracy of 0.1% (at a constant modulation angle of $\alpha = -45°$). This accuracy corresponds to a phase angle $\phi_m$ between the oscillation velocity and the excitation force, deviating by less than 0.5° from the optimum value $\phi_{opt}$. As already mentioned, the optimum value, at which the correct density results from equation (2), depends on the quality factor and is given by the formula (11).

Instead of indicating only the value $T_m$, the time intervals $t_1$ and $t_2$, or the values formed therefrom by division by N, may also be indicated and/or recorded in addition, and the quality factor may be computed therefrom. That is, the Q factor is given by the relation $$Q = \sqrt{2}\, \epsilon(t_1+t_2)/(t_2-t_1) \qquad (13)$$

wherein the already mentioned quantity $\epsilon$ is the amplitude ratio or mean value ratio between the two voltages which are superimposed in the modulator, i.e., between the fractions of voltage $U_{26}$ and $U_{27}$ formed in the modulator by voltage division. From the quality factor Q, in turn, the viscosity of the measured fluid can be calculated, which is also useful in some case. There is also a further possibility to produce, by means of a suitable computing circuit, an electric signal as a function of the quality factor. This signal may then be used for controlling a phase shifter in dependence on the quality factor. For example, the modulation angle $\alpha$ may be varied as a function of the quality factor. In this way, the optimal value of the phase positions could be adjusted still more exactly and, if necessary, the measuring accuracy could further be increased.

The described device thus makes it possible to measure the density, and also the quality factor and the viscosity, with a high accuracy. For densities between 0 and 3 g/cm³, the oscillation frequencies of the oscillating body range approximately between 0.5 and 5 kHz. The timing unit is advantageously designed to produce a signal, for controlling the modulator, having a frequency which is about 100 to 500 times lower than the oscillation frequencies, thus in the order of magnitude of Hz. If, in order to determine the density as described, the length of the modulation period is measured continuously, at least one measured value is obtained per second. Consequently, the density can be measured not only very accurately, but also quasi-continuously. This is frequently very advantageous in the processing technique or for measuring operations in pipelines.

Of course, other ways might also be considered to carry out the modulation and determine the period $T_m$ or the frequency reciprocal thereto. For example, a timer may be provided which is controlled not by the oscillation frequency of the oscillating body but by an oscillator producing a constant frequency. Also, it is not absolutely necessary to modulate with a rectangular-wave signal. In principle, phase angle $\phi$ might be varied otherwise, at least approximately periodically and in such a manner as to keep the intermediate value $\phi_m$ within the interval of variation. It might then be necessary to determine the period $T_m$ also somewhat differently.

Figure 9:
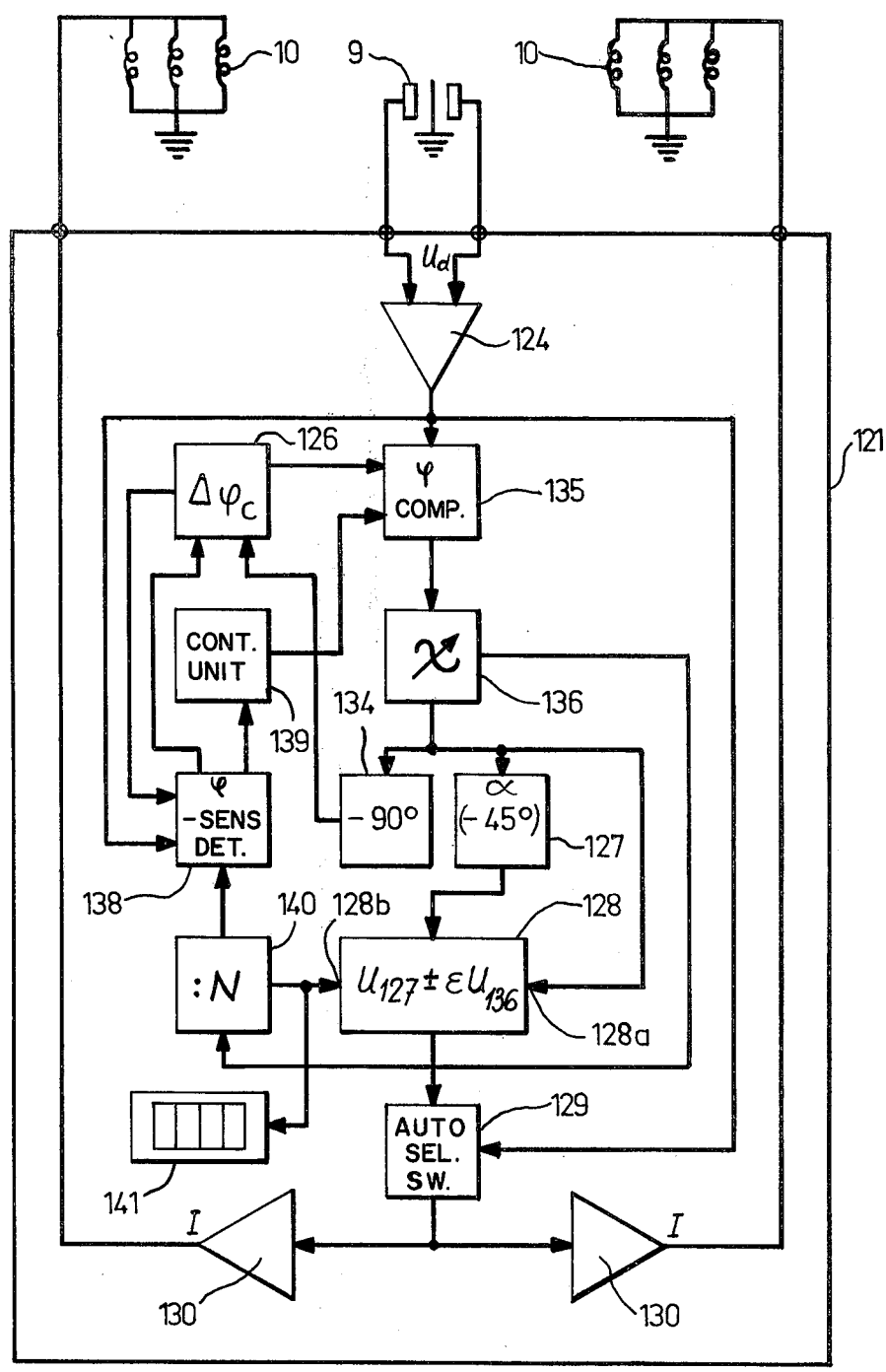
FIG. 9 is a block diagram of a variant of an electronic circuitry comprising a voltage-controlled oscillator.

Another embodiment of the electronic circuitry or component will now be explained with reference to FIG. 9. The electronic part 121 shown in FIG. 9 has terminals to which the oscillation detector 9 and the windings of the oscillation generators 10 are connected. Oscillation detector 9 is connected to the inputs of a differential amplifier 124 whose output is connected to a phase comparator 135. The output of the phase comparator is connected to a voltage-controlled oscillator 136 having its output connected to the inputs of two phase shifters 127 and 134. The output of phase shifter 127 is connected to the input of a modulator 128. The other terminal 128a of the modulator is connected to the output of oscillator 136. The output of modulator 128 is connected to the input of an automatic selector switch 129 whose output, in turn, is connected to two amplifiers 130 which serve as controllable current sources and have their outputs connected to the windings of oscillation generators 10. There are also provided a controllable phase shifter 126, a phase-sensitive detector 138, a control unit 139, a timer 140 and a period meter 141. The input of timer 140 is connected to one of the outputs of oscillator 136. Timer 140 comprises a frequency divider and its output is connected to the terminal 128b of the modulator and to period meter 141. One output of timer 140 is connected to one of the inputs of phase-sensitive detector 138 whose two further input terminals are connected to the output of differential amplifier 124 and to one output of phase shifter 126. One output of detector 138 is connected to one of the inputs of phase shifter 126. The other input of phase shifter 126 is connected to the output of phase shifter 134 producing a phase shift of $-90°$. The other output of phase shifter 126 is connected to phase comparator 135. The other output of phase-sensitive detector 138 is connected to the input of control unit 139 whose output connects to one output of phase comparator 135.

In operation, controllable oscillator 136 produces an alternating voltage having a definite frequency. Phase shifter 127 shifts the phase of the oscillator output voltage through a modulation angle $\alpha = -45°$. The output signal of phase shifter 127 is modulated, in modulator 128, with the rectangular-wave alternating voltage produced by the timer. Modulator 128, timer 140, period meter 141, selector switch 129, and amplifiers 130 operate substantially in the same manner as the corresponding elements of electronic part 21. Phase shifter 134 shifts the phase of the oscillator output voltage through $-90°$. The output voltage of phase shifter 134 is supplied, through controllable phase shifter 126, to phase comparator 135. The comparator compares the phase of the output voltage of differential amplifier 124 with the phase of the output voltage of phase shifter 126 and controls oscillator 136 in such a manner that the two last-mentioned voltages are in phase quadrature to each other. As long as controllable oscillator 136 produces an alternating voltage having ideal frequencies which depend on the quality factor and, of course, on the density of the fluid to be measured, the amplitude of the detector signal delivered by the oscillation detector remains constant during the modulation. However, if, during the modulation, the amplitude of the detector signal varies, detector 138 controls phase shifter 126 to the effect that the phase position of the output voltage of phase shifter 126 changes until the amplitude of the detector signal finally ceases to vary during the modulation. Analogously to detector 38 of the first embodiment, detector 138 is controlled by the timer in synchronism with the modulation.

The purpose of control unit 139 is, upon switching on the electronic part 121, to vary the frequency until the neighborhood of the resonance frequency is reached. As soon as the amplitude of the oscillation and, thereby, the detector signal have increased to a satisfactory magnitude, control unit 139 puts the control circuit in effect, whereupon, the control circuit adjusts the phase position in the above-described manner.

Thus, in both embodiments of the electronic component, a modulation takes place during which the phase angle between the excitation signal and the detector signal and the amplitude of the excitation signal are periodically varied in a predetermined manner. Further, in both embodiments, the phase position of the modulation interval is controlled, by means of a controllable phase shifter and further control elements, in such a way that the amplitude of the detector signal and, thereby, the amplitude z of the deflection remain constant during the modulation.

Instead of a piezoelectric detector, however, a detector with an induction coil might be provided. Then, the detector signal, i.e., the induced voltage, would not be proportional to the deflection, but to the oscillation velocity. In such a case, the electronic parts might be designed to keep constant the amplitude v of the oscillation velocity. For this purpose, only small changes had to be made in electronic components 21 and 121. These changes would result alone from taking into account the phase quadrature between the oscillation velocity and the deflection. Incidentially, in this case again, the quality factor might be determined and a phase angle correction made as a function of the magnitude of the quality factor.

However, it is not absolutely essential to design the electronic circuitry or component for keeping constant the amplitude of the deflection or of the oscillation velocity by the adjustment of an optimal phase angle. That is, modulators and control circuits may be provided making it possible to satisfy the differential equation (4a) or (5a) at least at one location within the modulation interval for a fixed modulation angle $\alpha$ or for a modulation angle depending on the quality factor, without the condition of both sides of the equation being identically equal to zero. However, in such cases again, the modulator must at least approximately periodically increase and reduce the phase angle. Thereby, the frequency is also necessarily varied, since the phase angle and the frequency are interconnected by the oscillation equation. Further, the modulation must be such that for a definite modulation angle $\alpha$ of about $-38°$ to $-50°$, preferably $-40°$ to $-45°$, the differential equation (4a) can be satisfied at least approximately. In the special case of $\alpha = -45°$, this means to satisfy differential equation (5a). Modulation angle $\alpha$ may be either fixed in advance or variable. As already mentioned, it would be possible to measure the quality factor directly, produce a corresponding electric signal, and use this signal for determining the value of $\alpha$. Then, the phase position of the modulation interval must be adjusted, by means of a controllable phase shifter, to at least approximately satisfy the differential equation (4a), or, in the special case, the differential equation (5a), within a partial interval of the modulation interval situated in the vicinity of $\alpha$.

Thus, in spite of the fact that the phase angle between the oscillation velocity or deflection and the excitation force cannot be determined with the necessary accuracy by means of static measurements and controls, a predetermined phase position can be adjusted accurately. This is done, summarily, by adjusting the position of a phase angle interval produced by modulation, at a difinite location of the interval, with respect to a relation between the differential values. In this way, the errors occurring in the static measurement and determination of phase angles can be eliminated, in practice, completely. But the oscillation values and their variations appearing in the equations (4) and (5) again cannot be ascertained and used for determining the condition of the oscillation directly. This can be done only through the associated electric signals. However, these variations as they appear in equations (4a) and (5a) can be determined, in practice, without errors. Now, if it is desired to verify in the finished device whether or not the equation (4a), or even the equation (5a), is actually satisfied, the variation in time of the detector signal and the excitation signal and of their amplitudes U and I within a modulation period $t_1 + t_2$ may be measured, for example, by means of an oscillograph. Therefrom, the values of the differentials can be determined for any location of the modulation interval. Even if the modulation is discontinuous, i.e., carried out by means of a rectangular-wave signal, as in the described embodiments, the results of the measurement make it possible to determine, i.e., calculate, the values of the differentials or their conditions for a differential region of modulation angle $\alpha$. The modulation angle $\alpha$ may be predetermined as a fixed value or, for example, as a function of the quality factor Q.

In the described embodiments, the modulator may have other functions but primarily modulates the phase, and a phase variation is also absolutely necessary. However, as follows from the solution of the differential equation of the oscillation and as has shortly been explained in connection with FIG. 4, variations of the phase angle are necessarily connected to the variations of the oscillation frequency, and, of course, also inversely. Thus, if a voltage-controlled oscillator is provided, as in electronic component 121, instead of primarily modulating the phase angle and the amplitude of the excitation signal, the frequency of the controlled oscillator might also be primarily modulated, i.e., periodically varied. That is, since with a definite design of the oscillating body and nature of the fluid to be measured, i.e., for any oscillation stage, the phase angle $\phi$ and the oscillation frequency clearly determine each other, any variation of frequency results in an exactly associated variation of the phase angle.

As already mentioned, instead of operating with detector signals representing the deflection due to the oscillation, it is possible to operate with signals representing the oscillation velocity, i.e., to use a detector with at least one induction coil, instead of a piezoelectric oscillation detector. Inversely also, instead of field coils, oscillation generators with piezoelectric crystals may be used. In this latter case, of course, the excitation signal is formed not by a current, but by a voltage, and accordingly, by the quantity I in equations (4a) and (5a), not a current but a voltage is to be understood.

It should further be noted that it is not absolutely necessary to determine the period $T_m$ or the frequency by averaging over the entire period of modulation. The timer and the modulator might also be designed and interconnected in such a manner that during a finite duration of a partial interval of each modulation period, the phase angle would have exactly the value of $\phi_m$. In such a case, the period meter might be controlled by the timer so as to measure only during the respective partial interval.

Finally, it is to be noted that the described modulation and control methods, of course, can be applied not only to plate-shaped oscillating bodies performing flexural oscillations, but also to other oscillating bodies and kinds of oscillation, for example, hollow oscillating cylinders of tuning forks.

While specific embodiments of the invention have been shown and described in detail to illustrate the application of the principles of the invention, it will be understood that the invention may be embodied otherwise without departing from such principles.

What is claimed is:

1. In a device for measuring the density of a liquid or gaseous medium, of the type including a support operable to hold an oscillation body, to be introduced into the medium, in a position permitting its oscillation, at least one oscillation detector operable to produce, during operation of the device, an electric detector signal in dependence on the oscillation of the oscillating body, at least one oscillation generator operable to excite the oscillating body, and an electronic circuitry component connected to the oscillation detector and the oscillation generator and including one of a period meter and a frequency meter, for determining one of the period and frequency of oscillation, and at least one phase shifter operable to supply the oscillation generator with an electric excitation signal shifted in phase, through a phase angle, relative to the detector signal produced by the oscillation detector: the improvement comprising, in combination, said electronic circuitry component comprising means operable to vary both the phase angle, between the detector signal and the excitation signal, and the oscillation frequency at least approximately periodically within an interval at a frequency which is less than the oscillation frequency of the oscillating body; and control elements operable to control the phase and frequency position of such interval as a function of the variation of the ratio of the detector signal to the excitation signal, and of the relation, within such interval, of the variations of the detector signal, the excitation signal, and the phase angle between the detector and excitation signals.

2. A device as claimed in claim 1, in which said electronic circuit component comprises a modulator operable to modulate at least the phase of an alternating signal supplied thereto.

3. A device as claimed in claim 2, in which said modulator and said control elements, during operation of said device, operate in a manner such that the position of the modulation interval is adjusted to satisfy, for a differential neighborhood of a location belonging to the modulation interval, at least approximately the relation $$dU/U = (dI/I) - tg\ \alpha \cdot d\Psi \qquad (4a)$$

wherein dU is the differential variation of the amplitude U of the detector signal, dI is the differential variation of the amplitude I of the excitation signal, d$\Psi$ is the differential variation of the phase angle $\Psi$ through which the detector signal is shifted relative to the excitation signal, and $\alpha$ is a phase angle having a magnitude between $-38°$ and $-50°$.

4. A device as claimed in claim 3, in which the magnitude of said phase angle is $-45°$.

5. A device as claimed in claim 3, in which said electronic circuit component includes a timing unit connected to said modulator and to said one of a period meter and a frequency meter; said timing unit being operable to control the elements connected thereto, during operation of said device, in a manner such that the length of the oscillation period of the oscillating body, which length is averaged over the entire modulation period, equals the length of the period of the oscillating body at said location of the modulation interval.

6. A device as claimed in claim 5, in which said timing unit produces a rectangular-wave signal; said electronic circuitry component including a phase shifter producing two alternating signals displaced relative to each other by a fixed phase angle and having a constant amplitude during the modulation; said modulator comprising means adding these two alternating signals to each other during one time interval of a modulation period, and for subtracting these two alternating signals from each other during another time interval of the modulation period, the addition and subtraction being effected in accordance with the rhythm of the rectangular-wave signal.

7. A device as claimed in claim 3, in which said control elements include a controllable phase shifter.

8. A device as claimed in claim 7, in which said control elements include means controlling the controllable phase shifter in a manner such that the amplitude of the detector signal remains constant during the modulation.

9. A device as claimed in claim 8, in which said control elements include a controllable amplifier connected in series to said controllable phase shifter; voltage control elements supplying said controllable amplifier with a control signal in a manner such that the amplitude of the output voltage of said controllable amplifier is maintained constant during the modulation; and a phase-sensitive detector connected to said voltage control means and to said timing unit and controlling said phase shifters in dependence on the magnitudes assumed by the control signal during such two time intervals of the modulation period.

10. A device as claimed in claim 1, in which said oscillation detector is a piezoelectric crystal producing, during operation of said device, a detector signal proportional to the deflection of the oscillating body.

* * * * *